United States Patent
Brattesani et al.

(10) Patent No.: US 6,766,809 B2
(45) Date of Patent: Jul. 27, 2004

(54) KEY-SHAPED FLOSS DISPENSER

(75) Inventors: Steven J. Brattesani, San Francisco, CA (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 92 days.

(21) Appl. No.: 10/082,699

(22) Filed: Feb. 25, 2002

(65) Prior Publication Data

US 2003/0159709 A1 Aug. 28, 2003

(51) Int. Cl.[7] .............................................. A61C 15/00
(52) U.S. Cl. .................... 132/325; 132/328; 362/116
(58) Field of Search ................... 132/321–329, 132/309; 70/456 R, 460, 458, 456 B

(56) References Cited

U.S. PATENT DOCUMENTS

| | | | | |
|---|---|---|---|---|
| 1,733,114 A | * | 10/1929 | Brennan | 132/314 |
| D293,491 S | | 12/1987 | Fronske | D28/64 |
| 4,787,016 A | * | 11/1988 | Song | 362/116 |
| 4,957,125 A | * | 9/1990 | Yaneza | 132/309 |
| 5,076,423 A | | 12/1991 | Russack | 206/63.5 |
| D329,137 S | | 9/1992 | Hinson | D3/62 |
| 5,417,232 A | * | 5/1995 | Ballard | 132/325 |
| 5,495,863 A | * | 3/1996 | Bergman | 132/326 |
| 5,544,754 A | * | 8/1996 | Stahl | 206/581 |
| 5,762,079 A | * | 6/1998 | Protonantis | 132/325 |
| 5,787,907 A | | 8/1998 | Endelson | 132/321 |
| 5,931,659 A | * | 8/1999 | Wu | 431/253 |
| 6,189,545 B1 | | 2/2001 | Tamez | 132/321 |

* cited by examiner

Primary Examiner—Kevin Shaver
Assistant Examiner—Stephanie L. Willatt
(74) Attorney, Agent, or Firm—Workman Nydegger

(57) ABSTRACT

Floss dispensers comprising a body configured for holding and dispensing floss and a gripping arm extending from the body configured to facilitate gripping by the user while floss is dispensed and cut from the dispenser. The body houses a spool of floss and includes a hole for dispensing the floss and a hole for connecting the floss dispenser to a key ring or chain. A floss cutter is included in the body or the gripping arm. In one embodiment the gripping arm comprises an operational key. The gripping arm is either integrally or removably connected with the body. In one embodiment, the body comprises a clam shell case configured to hold the head of a key. In another embodiment, the body comprises a sheath type pocket configured to hold the head of a key. The floss dispensers may also comprise other features, including lights and a toothpick.

23 Claims, 3 Drawing Sheets

KEY-SHAPED FLOSS DISPENSER

BACKGROUND OF THE INVENTION

1. The Field of the Invention

The present invention generally relates to the field of dental products and, more specifically, to floss dispensers.

2. The Relevant Technology

Personal oral and dental hygiene is important for many people, not only for maintaining healthy gums and teeth, but also for improving or eliminating bad breath and for removing unsightly food particles from between the teeth. Good personal oral and dental hygiene includes brushing and flossing of the teeth on a regular basis, preferably after eating. However, it can be inconvenient and impractical to carry around large containers of floss throughout the day to be used intermittently between the eating of snacks and meals. Accordingly, floss dispensers have been developed that are small enough to carry in a person's pocket.

One problem with small floss dispensers, however, is that because of their size, they can easy be overlooked and become lost when they are temporarily set down. Yet another problem associated with small floss dispensers is that they can be difficult to use. For example, it can be difficult to hold a floss dispenser that is very small while trying to remove and cut the floss from the dispenser. This is particularly true for people that have arthritis or other joint disorders that can affect manual dexterity.

Accordingly, there is currently a need in the art for improved floss dispensers.

SUMMARY OF PRESENTLY PREFERRED EMBODIMENTS

Briefly summarized, presently preferred embodiments of the present invention are directed to improved floss dispensers having support arms configured to be held and to provide support during use.

According to one embodiment, the floss dispenser includes a body configured for holding and dispensing floss and a gripping arm extending away from the body. The gripping arm generally provides a gripping handle for increased leverage while dispensing the floss and for cutting the floss from the dispenser. During use, the gripping arm can be held in a user's hand while the floss is pulled through a small hole in the body and cut on a cutter that is either connected to the body or the gripping arm.

According to one embodiment, the body of the floss dispenser may be configured with a hole suitable for connection to a key chain, key ring, and the like. This embodiment is useful for at least enabling the floss dispenser to be carried and used throughout the day, while at the same time minimizing the chances that the floss dispenser will be misplaced. The gripping arm can advantageously be configured in the shape of a key having teeth and other functional features suitable for operating a lock, or it may include merely ornamental teeth suitable for disguising the floss dispenser as an actual key, thereby enabling a person to carry the floss dispenser as discretely as possible. In this way, flossing can be surreptitious.

The gripping arm, which may be composed of any substantially rigid material, can be integrally connected to the body of the floss dispenser at the time of manufacture or, according to another embodiment, can comprise an actual key that is connected with the body of the floss dispenser by a mechanical means. For example, in one embodiment, the body of the floss dispenser comprises a casing having two body halves configured to open and close like a clam shell. According to this embodiment, the head of a key is securely held between the two body halves when the casing is closed. This embodiment is useful for enabling different keys to be interchangeably used, not only as a support arm, but also for pure key type operations such as for opening locks.

According to another embodiment, the body of the floss dispenser includes a sheath configured for receiving and securely holding the head of a key. This embodiment also enables different keys to be interchangeability used as a support arm and for true key functionality. The sheath may advantageously comprise rubber or another type of material with a high coefficient of frictional for securing the key in place against the body of the floss dispenser. In the alternative, the body of the floss dispenser may be clamped firmly together in a vice-like fashion around the key head by, e.g., one or more set screws.

According to yet another embodiment, the body of the floss dispenser can be configured to incorporate other devices for additional utility. For example, the body of the floss dispenser can be equipped with a small light to be used for illumination. The body of the floss dispenser can be equipped with a small toothpick for removing debris from between the teeth prior or subsequent to flossing.

It will be appreciated that the floss dispenser of the invention is generally useful for facilitating the removal of floss from the dispenser. In particular, the floss dispenser is configured for being held or gripped by the gripping arm while floss is dispensed and cut from the dispenser. The floss dispenser is also configured for being attached to a key chain so that it can be carried around at all times without being misplaced or lost.

These and other benefits, advantages and features of the present invention will more fully apparent from the following description and appended claims, or may be by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the floss dispensers of the invention will now be provided with specific reference to figures illustrating various embodiments of the invention. It will be appreciated that like structures will be provided with like reference designations.

The embodiments of the present invention are generally directed to improved floss dispensers that include a body and a support arm protruding away from the body. The body is configured to hold and dispense floss and the support arm is configured to provide support while dispensing the floss. The support arms can also be configured with cutting devices for cutting the floss once dispensed.

Figure 1:
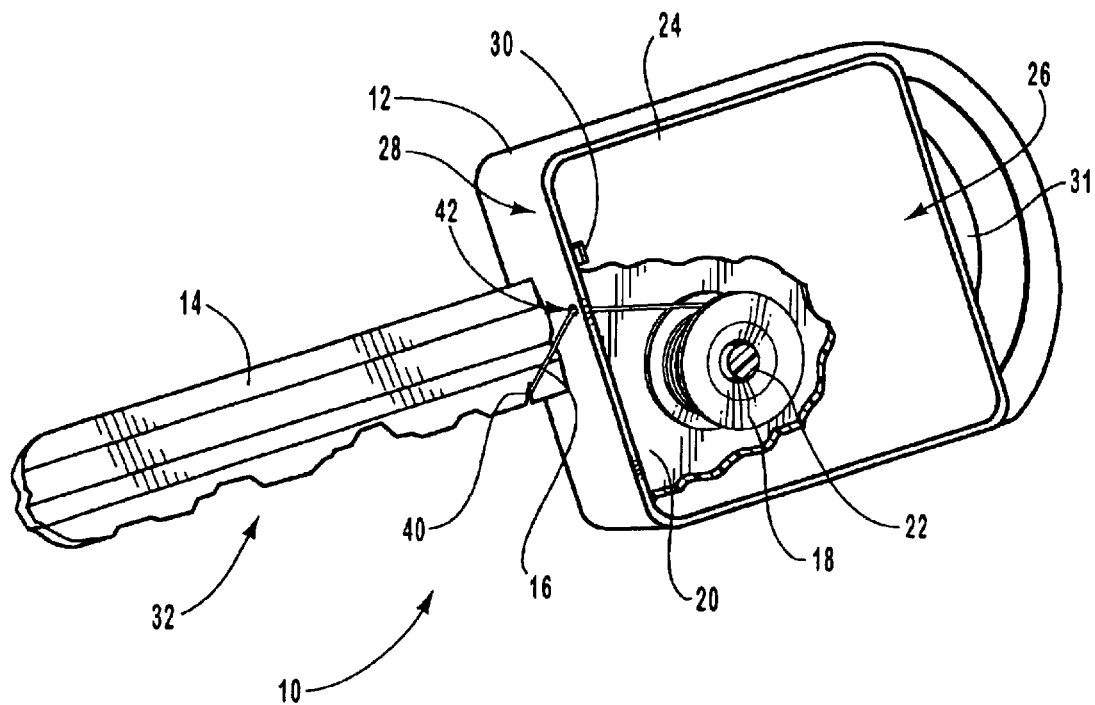
FIG. 1 illustrates a cut-away perspective view of one embodiment of the floss dispenser of the invention that includes a body, a floss spool and a key-shaped gripping arm.

Reference is first made to FIG. 1, which illustrates a perspective view of one embodiment of the floss dispenser of the invention. As shown, the floss dispenser 10 includes a body 12 and a gripping arm 14. The body 12 and gripping arm 14 can be manufactured out of any suitable material including, but not limited to, plastic, ceramic or metal. In one embodiment, the body 12 and the gripping arm 14 are integrally connected at the time of manufacture such as, for example, during casting or molding. The gripping arm 14 can also be attached to the body 12 subsequent to manufacture such as, for example, by a welding process, using an adhesive, or by means of a set screw (not shown).

The body 12 is specifically configured for holding and dispensing dental floss 16. The dental floss 16 may be dispensed, for example, from a spool 18 that is attached within a hollow cavity 20 of the body 12. The spool 18 is preferably mounted on a spool rod 22, which enables the spool 18 to freely rotate within the body 12, such as when the dental floss 16 is pulled through a dispensing hole 42 through the body.

The spool 18 can be placed within the hollow cavity 20 of the body 12 at any appropriate time during manufacture of the body 12. For example, the spool 18 can be placed within the body 12 after manufacture by providing a cover 24 on the body 12 that can be opened and closed. According to one embodiment, the cover 24 can be hingedly attached to the body at a first side 26 and frictionally closed at a second side 28. The cover 24 can be opened by prying the cover 24 away from the body 12 at the second side 28. To assist in the opening of the cover 24, a recess may be provided, such as recess 30, for inserting a tool that can pry open the cover 24. Although the previous example has gone into some detail regarding how the cover 24 can be opened, it will be appreciated that any suitable means can be used for opening and closing the cover 24, when necessary, for placing the spool 18 of floss 16 within the body 12. For example, a set screw may be provided that locks and unlocks the cover 24 to the body 12. In other embodiments, the cover 24 may be permanently closed once the spool 18 has been placed within the body 12.

As shown in FIG. 1, the gripping arm 14 extends away from the body 12 of the floss dispenser 10, which enables it to be used for gripping or support during use. In particular, the gripping arm 14 can be held or gripped by the user during use for providing additional support and stability while the floss 16 is pulled and cut away from the dispenser 10. It will be appreciated that this is an improvement over other small floss dispensers that can be difficult to use, particularly for people suffering joint and dexterity disorders.

Some existing floss dispensers are also so small that they can be easily misplaced, overlooked and lost. The floss dispensers of the present invention generally overcome this problem by providing a body 12 configured with a hole 31 for being attached to a key chain, a necklace, or any other object that is not likely to be misplaced. It will be appreciated that this generally facilitates carrying the floss dispenser throughout the day, which can be useful for enabling a person to floss between meals to maintain good personal hygiene and good breath.

According to one embodiment, the gripping arm 14 may be configured in the shape of a key. This is useful for disguising the floss dispenser 10 as a key, thereby enabling a person to carry the floss dispenser 10 discretely, when desired, thereby enabling surreptitious flossing of the person's teeth. The key shape of the gripping arm 14 can also be useful when the gripping arm 14 is composed of a metal. In particular, teeth 32 can be cut into the support arm 14, thereby enabling the support arm 14 to be utilized as a working key. Methods and devices for cutting teeth in keys are well known in the art. It will be appreciated, however, that the operable key function of the gripping arm 14 is not limited to opening mechanical locks. In particular, the gripping arm 14 may also comprise electronic or magnetic codes configured to open electronic and magnetic locks. The gripping arm 14 may be entirely decorative if desired.

According to one embodiment of the invention, the gripping arm 14 may include a cutting groove 40 configured for cutting the floss 16 once it is pulled from the body 12 through the floss dispensing hole 42. The cutting groove 40 may be configured to hold the floss 16 in place after it is cut, as shown or, alternatively, the gripping arm 14 may simply comprise a sharp edge that is used only to cut the floss 16. For example, teeth 32 formed in the gripping arm 14 can comprise a cutter used to cut the floss 16. When the cutting groove 14 is not configured to hold the main floss strand 16 in place upon being cut, it may be useful, according to one embodiment, for the floss-dispensing hole 42 to be very small so that the floss 16 can be frictionally held in place by the walls of the hole 42. This is useful, for example, to prevent the floss 16 from retracting through the hole 42 into the cavity 20 of the floss dispenser 10.

Figure 2:
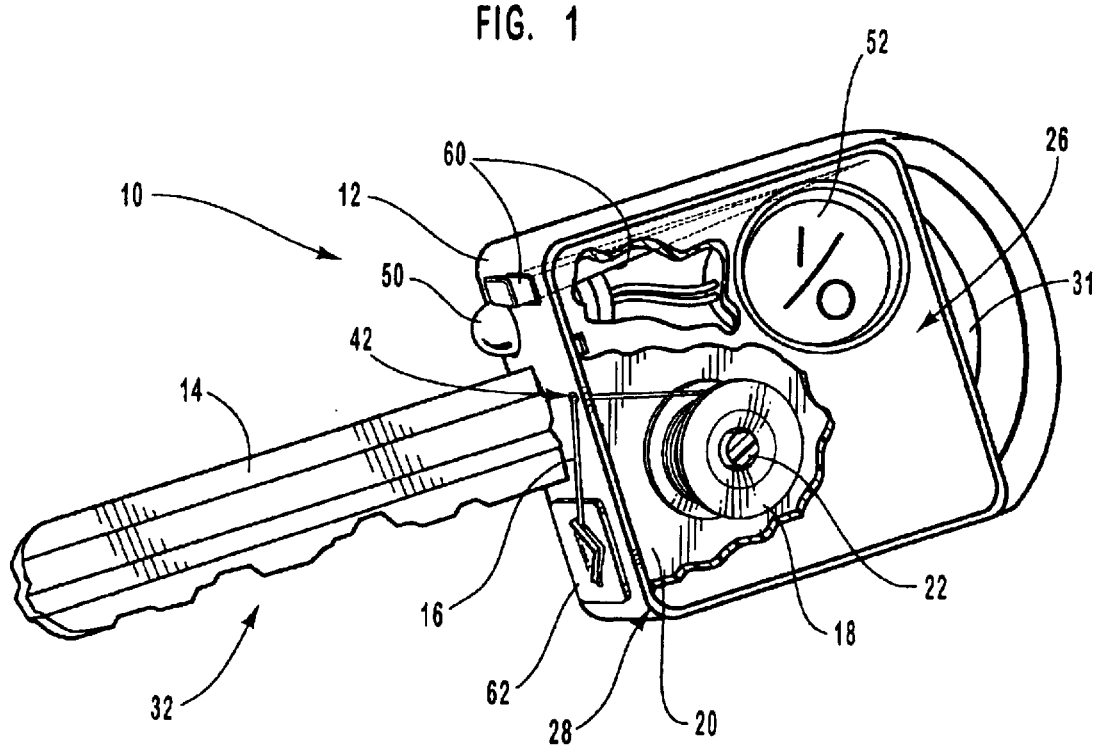
FIG. 2 illustrates an alternative cut-away view of the floss dispenser shown in FIG. 1.

Turning now to FIG. 2, it is shown how the floss dispenser 10 can include other useful components. For example, the floss dispenser 10 can include a light 50 (e.g., an LED or incandescent light), which is illuminated when a button 52 is depressed. The light 50 can be particularly useful for illuminating a lock when the gripping arm 14 comprises a workable key that is being inserted into a lock (not shown). The light is also useful for illuminating other objects, even when the support arm 14 does not comprise a workable key.

A toothpick 60 is yet another object that can be included with the floss dispenser of the invention. For instance, according to the embodiment shown in FIG. 2, the body 12 of the floss dispenser 10 is configured to hold a toothpick 60 therein that may be used to remove food particles from between the teeth, either before or after flossing to complete the dental hygiene process. The body 12 of the floss dispenser 10 can also be configured with a floss cutter 62. The floss cutter 62 can be integrally formed into the body 12 at the time of manufacture or, alternatively, as shown, the floss cutter 62 may comprise a separate device that is affixed to the body 12. The floss cutter 62 can be affixed to the floss dispenser 10 with adhesives, by welding, or by any other suitable means.

Figure 3:
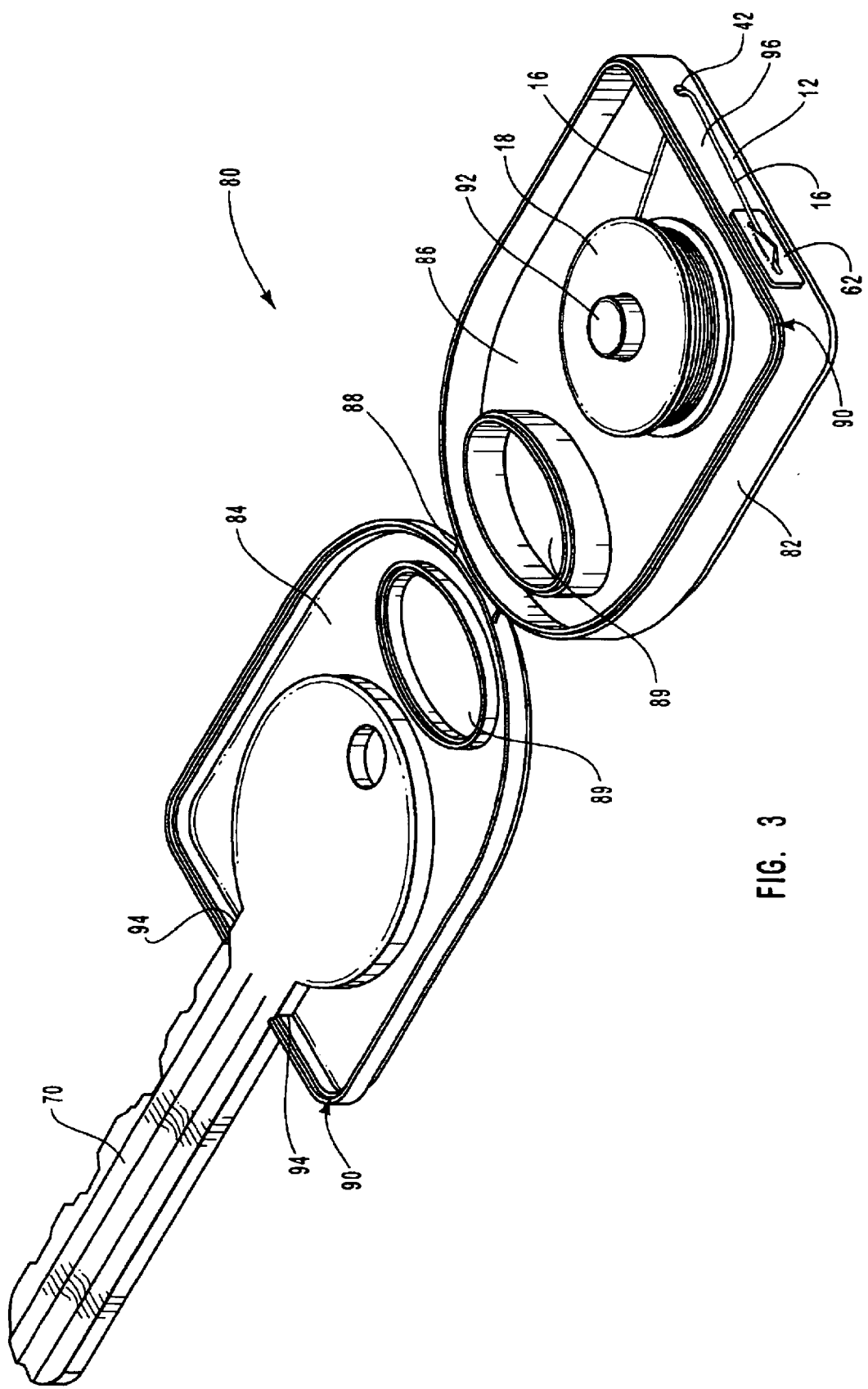
FIG. 3 illustrates a perspective view of one embodiment of the floss dispenser including two body halves that are hinged together and a gripping arm comprising an actual key.

Turning now to FIG. 3, it is shown how, according to one embodiment, the gripping arm of the floss dispenser 80 comprises an actual key 70 that is partially inserted within the body 82 of the floss dispenser 80. According to this embodiment, the body of the floss dispenser 80 comprises two body halves 84, 86 that are hingedly connected together, such as with a plastic hinge 88. The floss dispenser 80 also includes latching mechanisms 90 configured for holding the two body halves 84, 86 closed, although other closure means can also be used. When the body halves 84, 86 are closed, the floss dispenser 80 appears similar to the floss dispenser 10 shown in FIG. 1.

The floss dispenser 80 generally includes the basic components that are described above in reference to FIG. 1, namely, a spool 18 of floss 16, a floss-dispensing hole 42, holes 89 configured for attaching the floss dispenser 80 to a key chain (not shown), and a floss cutter 62. The floss dispenser 80 also includes a key retention pin 92. The key retention pin 92 generally operates as an axle for holding the key 70 securely in place once the two body halves 84, 86 have been closed together. The key retention pin 92 also operates as rotation axle about which the spool 18 of floss 16 can rotate during use.

As shown, body half 84 includes walls 94 configured to receive and mechanically engage the sides of the key 70, which is useful for holding the key 70 in place until the two body halves 84, 86 are closed together. Once the floss dispenser 80 is closed, the walls 94 of body half 84, the key retention pin 92, and the front wall 96 of body half 92 hold the key 70 securely in place so that the key can function as a gripping arm, as generally described above.

Figure 4:
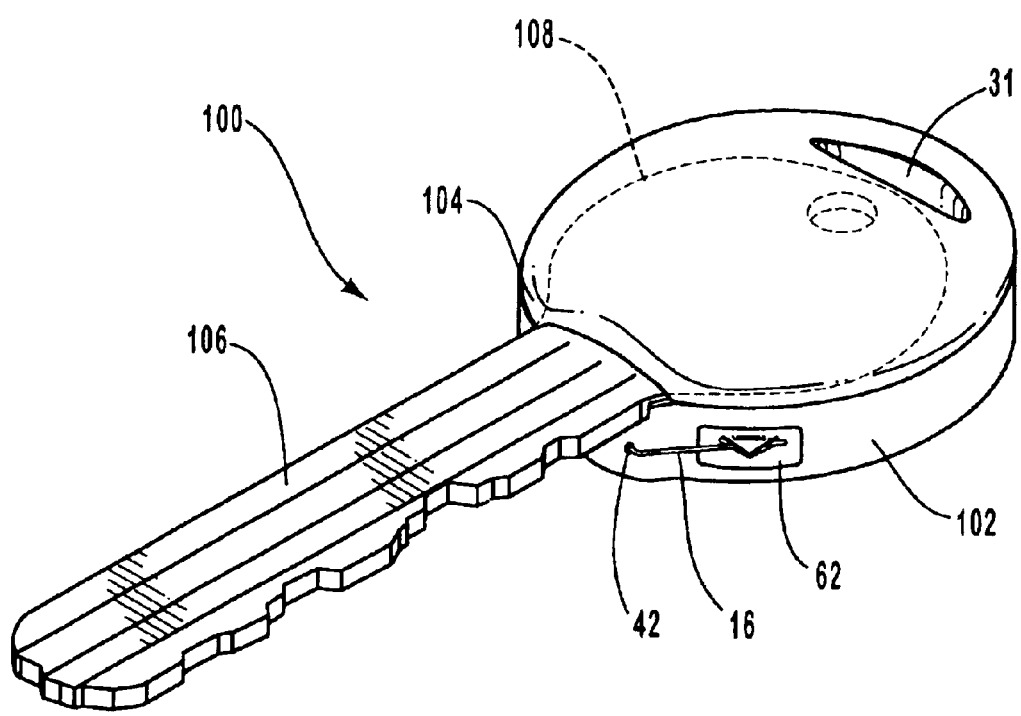
FIG. 4 illustrates a perspective view of one embodiment of the floss dispenser that includes a body with a sheath and a gripping arm comprising a key that is secured within the sheath.

Turning now to FIG. 4, another embodiment of the floss dispenser 100 of the invention is shown. In this embodiment, the body 102 of the floss dispenser 100 is configured with a sheath 104 suitable for securing the support arm 106 in place against the body 102. In the present embodiment, the support arm 106 comprises a key that is securely held in place when the head 108 of the key is placed within the body 102 of the floss dispenser 100 and covered with sheath 104.

The sheath 104 is preferably composed of a material with a high coefficient of friction. This is generally useful for holding the support arm 106 in place. The sheath 104 may, for example, be composed of rubber or other elastomers. Although other materials can also be used, rubber is a particularly good material because it can stretch when the head 108 of the key is placed between the sheath 104 and body 102, thereby enabling keys with differently shaped heads to be incorporated within the floss dispenser 100 of the invention.

The floss dispenser 100, as in previous embodiments, also includes a floss-dispensing hole 42 and a floss cutter 62 configured for cutting the floss 16 once dispensed, and a hole 31 for connection with a key ring. Although not shown, the floss dispenser 100 also includes a spool of floss that is housed within the body 102 of the floss dispenser 100.

Although specific embodiments of the floss dispensers of the invention have been illustrated and described herein, it will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A floss dispenser comprising:
   a body configured to hold and dispense dental floss,
      the body comprises two parts that are selectively separable and that together define a cavity for holding dental floss prior to being dispensed, the body further including a hole configured for connection to a key ring or chain; and
   an arm extending away from the body, the arm configured so as to facilitate gripping by a user when removing dental floss from the body,
      a portion of the arm being selectively received and held within the cavity when the two parts of the body are connected together.

2. A floss dispenser as recited in claim 1, further comprising a spool of dental floss rotatably connected within a cavity of the body.

3. A floss dispenser as recited in claim 2, wherein the spool of dental floss is refillable.

4. A floss dispenser as recited in claim 1, wherein the arm comprises a key.

5. A floss dispenser as recited in claim 4, wherein the key comprises teeth configured for operating a lock.

6. A floss dispenser as recited in claim 4, wherein the key comprises a decorative key arm.

7. A floss dispenser as recited in claim 1, further comprising a cutting device configured for cutting floss.

8. A floss dispenser as recited in claim 7, wherein the cutting device is disposed on the body.

9. A floss dispenser as recited in claim 7, where in the cutting device is disposed on the arm.

10. A floss dispenser as recited in claim 1, further comprising a light and a button mounted on the body, the button being configured for operating the light.

11. A floss dispenser as recited in claim 1, wherein the body and arm comprise at least one of a plastic or metal.

12. A floss dispenser as recited in claim 1, wherein the body is further includes a floss dispensing hole.

13. A floss dispenser as recited in claim 1, further comprising a toothpick removably disposed in or on the body.

14. A floss dispenser comprising:
   a body configured to hold and dispense dental floss;
   an arm extending away from the body, the arm configured so as to facilitate gripping by a user when removing dental floss from the body; and
   a light and a button mounted on the body, the button being configured for operating the light.

15. A floss dispenser as recited in claim 14, wherein the arm comprises an operable key having a head.

16. A floss dispenser as recited in claim 15, wherein the body two body halves, wherein the body halves are configured for securely holding the head of the key there between.

17. A floss dispenser comprising:
   a body;
   an attachment hole within the body configured for attachment of the body to a key ring or chain;
   a spool of dental floss disposed within a cavity of the body;
   a floss-dispensing hole disposed through a side of the body; and
   a key connected to the body, the key including a head disposed within a cavity of the body and an arm extending from the body that facilitates gripping by the user when removing dental floss from the body through the floss dispensing hole.

18. A floss dispenser comprising:
   a body configured to hold and dispense dental floss; and
   an arm extending away from the body, the arm comprising a key and configured so as to facilitate gripping by a user when removing dental floss from the body.

19. A floss dispenser as recited in claim 18, wherein the key comprises teeth configured for operating a lock.

20. A floss dispenser as recited in claim 18, wherein the key comprises a decorative key arm.

21. A floss dispenser as recited in claim 18, wherein the arm is integrally connected with the body.

22. A floss dispenser as recited in claim 18, wherein the arm is mechanically connected with the body.

23. A floss dispenser comprising:
- a body configured to hold and dispense dental floss, the body comprising two parts that are selectively and that together define a cavity for holding dental floss prior to being dispensed;
- an arm extending away from the body, the arm configured so as to facilitate gripping by a user when removing dental floss from the body,
- a portion of the arm being selectively received and held within the cavity when the two parts of the body are connected together; and a toothpick removably disposed in or on the body.

* * * * *

UNITED STATES PATENT AND TRADEMARK OFFICE
CERTIFICATE OF CORRECTION

PATENT NO. : 6,766,809 B2
DATED : July 27, 2004
INVENTOR(S) : Steven J. Brattensani and Bruce S. McLean It is certified that error appears in the above-identified patent and that said Letters Patent is hereby corrected as shown below:

Column 2,
Line 35, after "invention will" insert -- become --
Line 36, after "or may be" insert -- learned --

Signed and Sealed this

Eighteenth Day of January, 2005

JON W. DUDAS
*Director of the United States Patent and Trademark Office*